US012714816B2

(12) United States Patent
Beckham et al.

(10) Patent No.: US 12,714,816 B2
(45) Date of Patent: Aug. 25, 2026

(54) ANTI-KINK AND ERGONOMIC NASAL CANNULA DEVICE

(71) Applicants: Diana Matthews Beckham, Saint Charles, MO (US); Charles E. Beckham, III, Saint Charles, MO (US)

(72) Inventors: Diana Matthews Beckham, Saint Charles, MO (US); Charles E. Beckham, III, Saint Charles, MO (US)

( * ) Notice: Subject to any disclaimer, the term of this patent is extended or adjusted under 35 U.S.C. 154(b) by 1239 days.

(21) Appl. No.: 17/516,567

(22) Filed: Nov. 1, 2021

(65) Prior Publication Data

US 2022/0160984 A1 May 26, 2022

Related U.S. Application Data

(60) Provisional application No. 63/108,404, filed on Nov. 1, 2020.

(51) Int. Cl.

| | |
|---|---|
| ***A61M 16/06*** | (2006.01) |
| ***A61M 16/00*** | (2006.01) |
| ***A61M 16/04*** | (2006.01) |
| ***A61M 16/08*** | (2006.01) |
| ***A61M 16/10*** | (2006.01) |
| ***A61M 16/16*** | (2006.01) |

(52) U.S. Cl.

CPC .... *A61M 16/0666* (2013.01); *A61M 16/0003* (2014.02); *A61M 16/0683* (2013.01); *A61M 16/0816* (2013.01); *A61M 2016/0027* (2013.01); *A61M 2205/02* (2013.01); *A61M 2210/0662* (2013.01); *A61M 2230/435* (2013.01); *A61M 2230/63* (2013.01)

(58) Field of Classification Search

CPC ................. A62B 18/02; A62B 18/025; A61M 16/0666–0891

See application file for complete search history.

(56) References Cited

U.S. PATENT DOCUMENTS

| | | | | |
|---|---|---|---|---|
| 4,949,733 A * | 8/1990 | Sampson | .......... | A61M 16/0672 128/864 |
| 2003/0189492 A1* | 10/2003 | Harvie | ............. | A61M 16/0051 340/611 |
| 2008/0142019 A1* | 6/2008 | Lewis | ............... | A61M 16/0677 128/207.18 |
| 2014/0364758 A1* | 12/2014 | Schindhelm | ...... | A61M 16/0633 128/204.22 |
| 2020/0276364 A1* | 9/2020 | Gandola | .............. | A61B 5/6834 |
| 2021/0046265 A1* | 2/2021 | Obenchain | ........ | A61M 16/0666 |
| 2021/0077765 A1* | 3/2021 | Peiris | .................. | A61M 16/161 |
| 2021/0290882 A1* | 9/2021 | Concklin | .......... | A61M 16/0683 |
| 2023/0031613 A1* | 2/2023 | Fleury | .................. | A61B 5/6803 |

* cited by examiner

*Primary Examiner* — Valeie L Woodward
*Assistant Examiner* — Mautin I Ashimiu
(74) *Attorney, Agent, or Firm* — Doster Greene, LLC

(57) ABSTRACT

A nasal cannula device according to various embodiments can include a flexible tube, an anti-kink device, and an ear protection device. The anti-kink devices may be attached to or integral with the distal end of the flexible tube that connects to a connection adapter, so that the anti-kink device provides support to the flexible tube to prevent kinking of the flexible tube. The ear protection device may be attached to or integral with a portion of the flexible tube that contacts a user's ear. The ear protection device comprises a soft material to mitigate skin irritation of the user's ear.

19 Claims, 14 Drawing Sheets

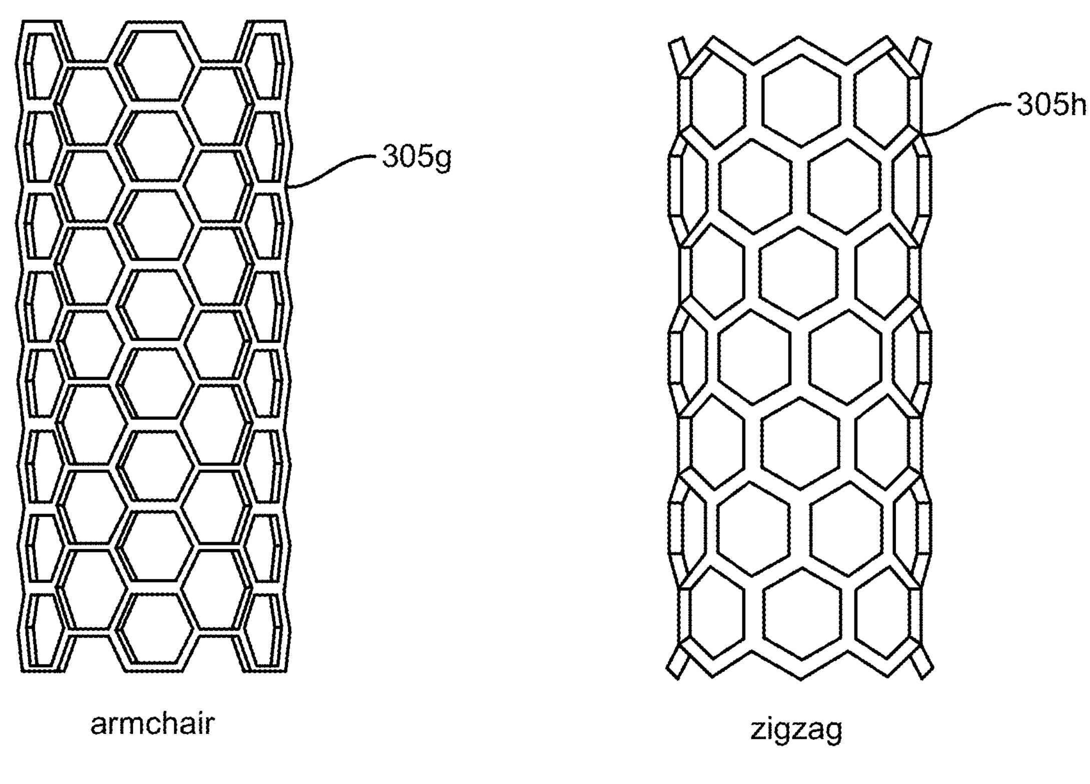
FIG. 7A
FIG. 7B
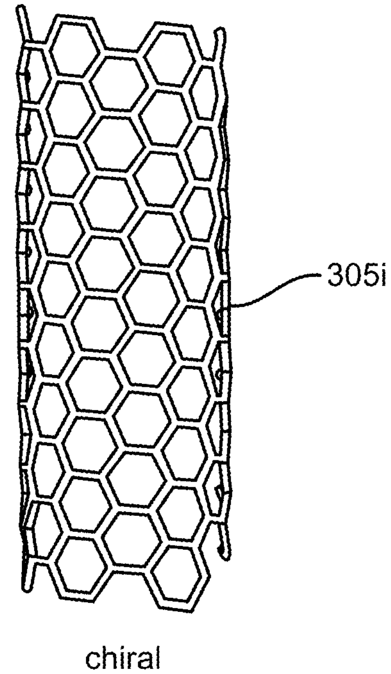
FIG. 7C

ANTI-KINK AND ERGONOMIC NASAL CANNULA DEVICE

CROSS-REFERENCE TO RELATED APPLICATIONS

This application claims benefit to U.S. Provisional Patent Application No. 63/108,404, filed Nov. 1, 2020, which is incorporated by reference herein in its entirety.

FIELD OF THE INVENTION

The present teachings relate generally to a nasal cannula device and, more particularly to an anti-kink nasal cannula device comprised of at least one or more ergonomic components to provide comfort to the user during use.

BACKGROUND

Oxygen is the primary fuel for the body. Every organ needs oxygen to work. If a person's body oxygen level gets too low the person's organs may start to actually shut down and even begin to be injured by lack of oxygen. Eventually, the person's organs can be permanently damaged or may be fatal if the person's oxygen level is low enough, long enough.

Oxygen therapy is usually delivered as a gas via an oxygen source. The oxygen is breathed through a nasal cannula or mask that covers the mouth and nose. The nasal cannula delivers oxygen through two small prongs that rest in the user's nostrils and leads to clear plastic tubing that hooks over the user's ears to be held in place and meets below the user's chin. The gas travels up through the nose and then down into the back of the throat where it is inhaled by the patient. Just normal breathing brings the extra oxygen into the lungs. The tubing is hooked up to one of several types of oxygen gas supply sources. The oxygen can come from a tank of concentrated oxygen 100 (FIG. 1A), an oxygen concentrator 105 (FIG. 1B), or from liquid oxygen. Typically, the device is used to deliver low flow levels of oxygen, but there are also high-flow nasal cannulas.

The normal practice is to adjust oxygen flow for patients to be comfortably above an oxygen blood saturation of 90% at rest. With advances in medical technology, oxygen delivery sources with mobility and portability have been enabled through the use of portable oxygen tanks. It is often, however, the case that patients need more oxygen for mobility or exercise. For example, a patient may use 2 L/min oxygen at rest but need 4 L/min with exertion.

However, one disadvantage associated with portable oxygen tanks is because the tube is flexible, normal movement of the user can result in the tube being blocked or restricted owing to kinking, bending, or twisting. Using a shoulder strap portable oxygen tank 110 or being active while wearing oxygen tubing can cause kinking of the tube. The tubing typically kinks where the softer tubing connects to the harder plastic female connector portion that connects to the portable oxygen tank. This connector is commonly known as a "Christmas tree" or nipple adapter 115, which is depicted in FIGS. 1A, 2A, and 2B.

The Christmas tree adapter 115 is used to attach the oxygen tubing 120 to the oxygen source. The Christmas tree adapter 115 includes grooved barbs 125 over which the oxygen tube 120 slides. The oxygen tube 120 can be twisted, bent, or become kinked at or adjacent to the Christmas tree adapter 115.

Many conventional portable oxygen tanks (FIG. 1A) or oxygen concentrators (FIG. 1B) are carried by a shoulder strap 130 to hang at a patient's side (FIG. 1B) or sit inside a backpack. Most of these conventional portable oxygen delivery devices have the connector nozzle of the Christmas tree adapter 115 positioned such that the connector nozzle 135 connects to the source and points in an upward direction such that the barbs 125 functions as a male portion. Then, a female portion 140 of a nasal cannula/oxygen tubing 120 is connected to the upward facing male portion 125. Commonly, kinking occurs in the connection area 145 between the harder plastic female connector 125 and the softer plastic oxygen tube 120 that delivers oxygen to the patients nose, mouth, or both. Kinking can occur because the connector nozzle 135 is facing upward or outward position, and the tubing 120 can be tugged, bumped, squeezed, or compressed by the patient's arm, causing a kink.

Whenever the tubing kinks, it limits the oxygen flow from the tank to the user, therefore potentially significantly causing a decrease in oxygen saturation for the person receiving the oxygen flow. Oftentimes, the patient needs the portable tank for mobility, which will most likely also require a higher oxygen demand due to exertional activity. A kink in the oxygen tube will restrict the oxygen flow and possibly be harmful to the user. The potential for oxygen tube kink is particularly prevalent in the connection area 145, which is adjacent to the connection 140 of the oxygen tube 120 to the Christmas tree adapter 115. Obviously, even one kink in the oxygen tube can significantly limit the effectiveness of the portable oxygen kit. This makes it even more crucial to address the tubing kink problem.

Another disadvantage associated with portable oxygen kits that is exacerbated by the user's movement is skin irritation. Some patients struggle with the problem of skin irritation, chafing, or even skin breakdown on the back of their ears due to prolonged or long-term oxygen nasal cannula use or mask wearing resulting in pressure on the sensitive parts of the back of the ears.

Thus, it is desirable to provide a portable oxygen system that effectively conveys oxygen to the user through an oxygen tube that is capable of twisting, bending, and blowing of the oxygen flow therethrough, without kinking, especially when the user has a greater need for oxygen during times of exertion.

It is also desirable to provide a portable oxygen system that solves the discomfort and mitigates skin irritation from the oxygen tube being looped over the user's ears.

It is further desired to monitor and adjust the oxygen level to maintain the oxygen supply delivered to the user during movement and exertion.

BRIEF DESCRIPTION OF THE DRAWINGS

FIG. 7A illustrates an exemplary embodiment of an anti-kink device having an armchair configuration in accordance with the present invention.

FIG. 7B illustrates an exemplary embodiment of an anti-kink device having a zigzag configuration in accordance with the present invention.

FIG. 7C illustrates an exemplary embodiment of an anti-kink device having a chiral configuration in accordance with the present invention.

DESCRIPTION

Figure 1A:
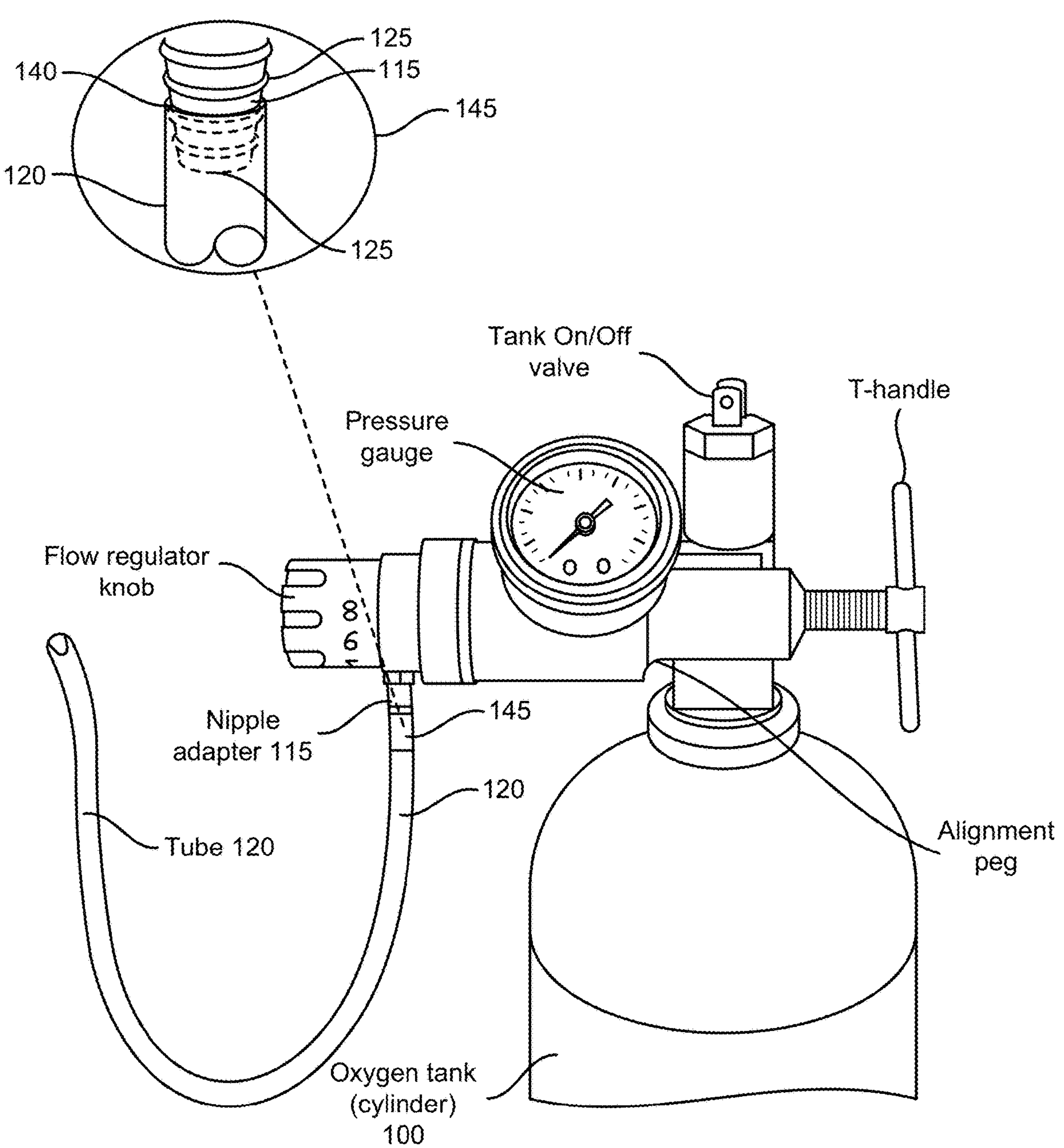
FIG. 1A illustrates an oxygen tank apparatus according to the prior art.
Figure 1B:
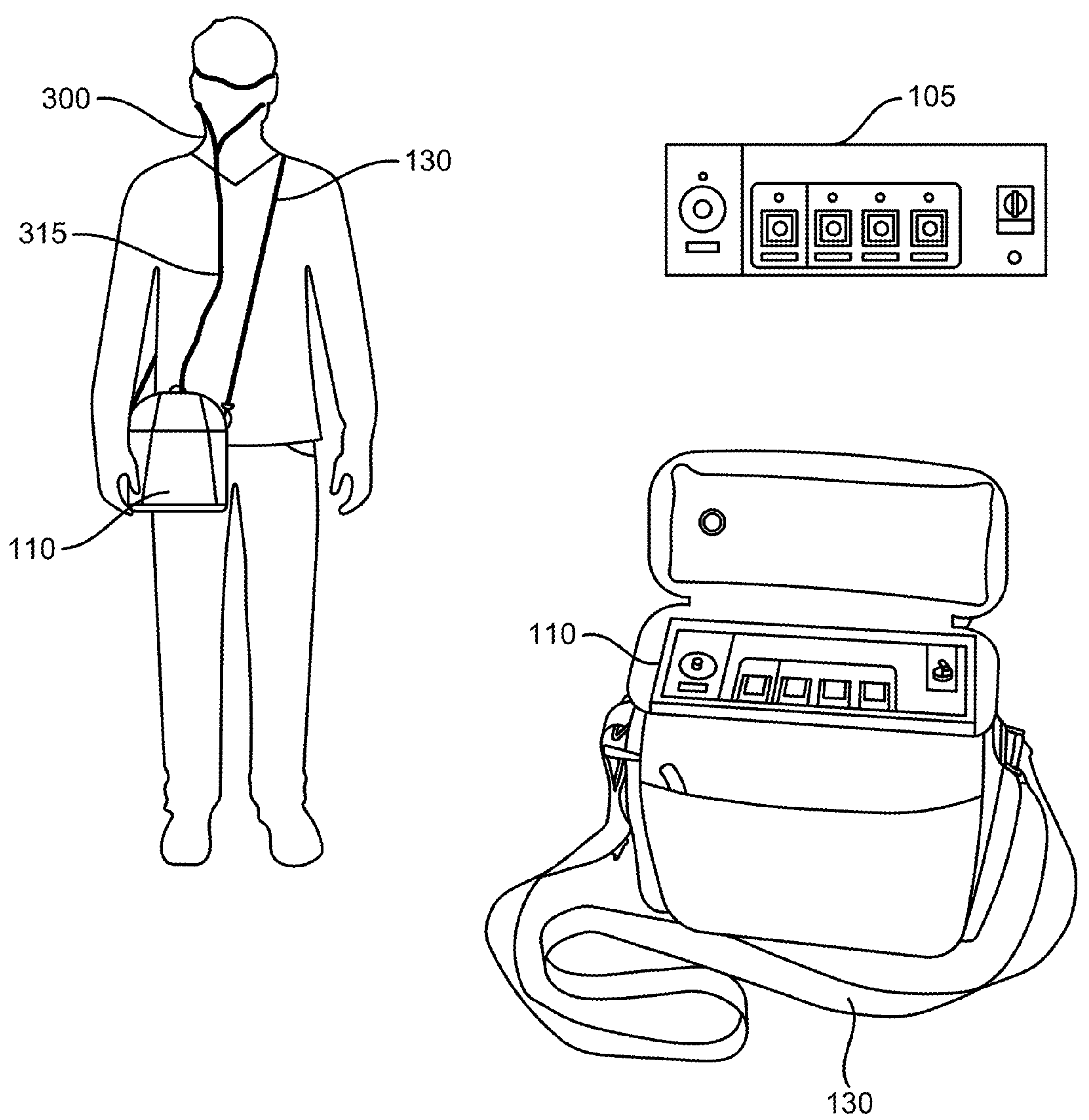
FIG. 1B illustrates a portable oxygen concentrator according to the prior art.
Figure 2A:
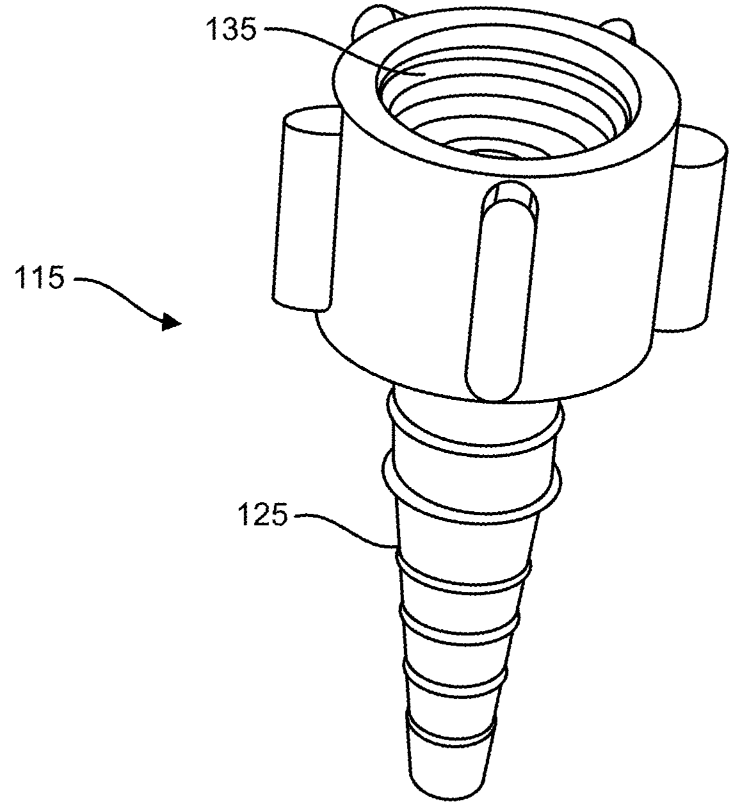
FIGS. 2A-2B illustrate a Christmas tree adapter or a nipple adapter according to the prior art.
Figure 2B:
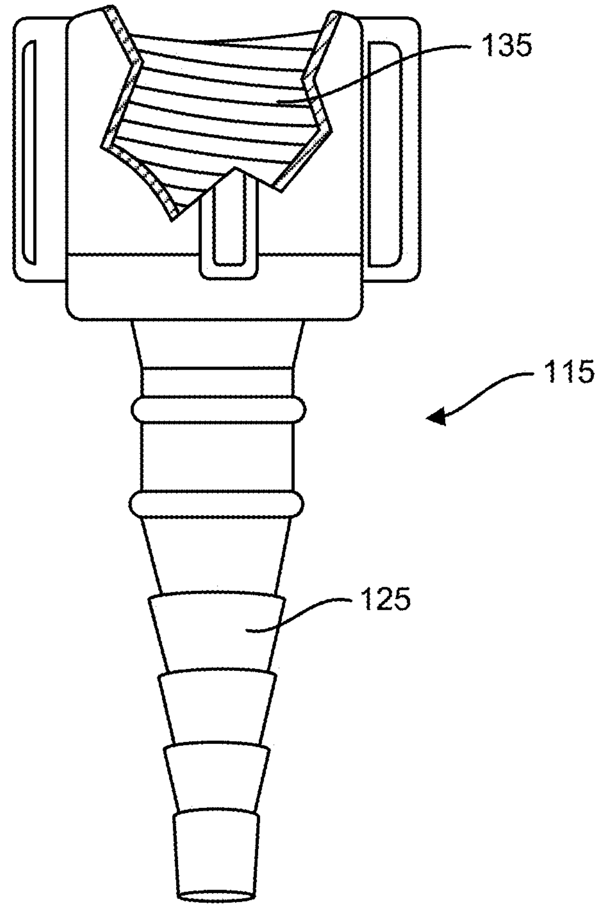
Figure 3:
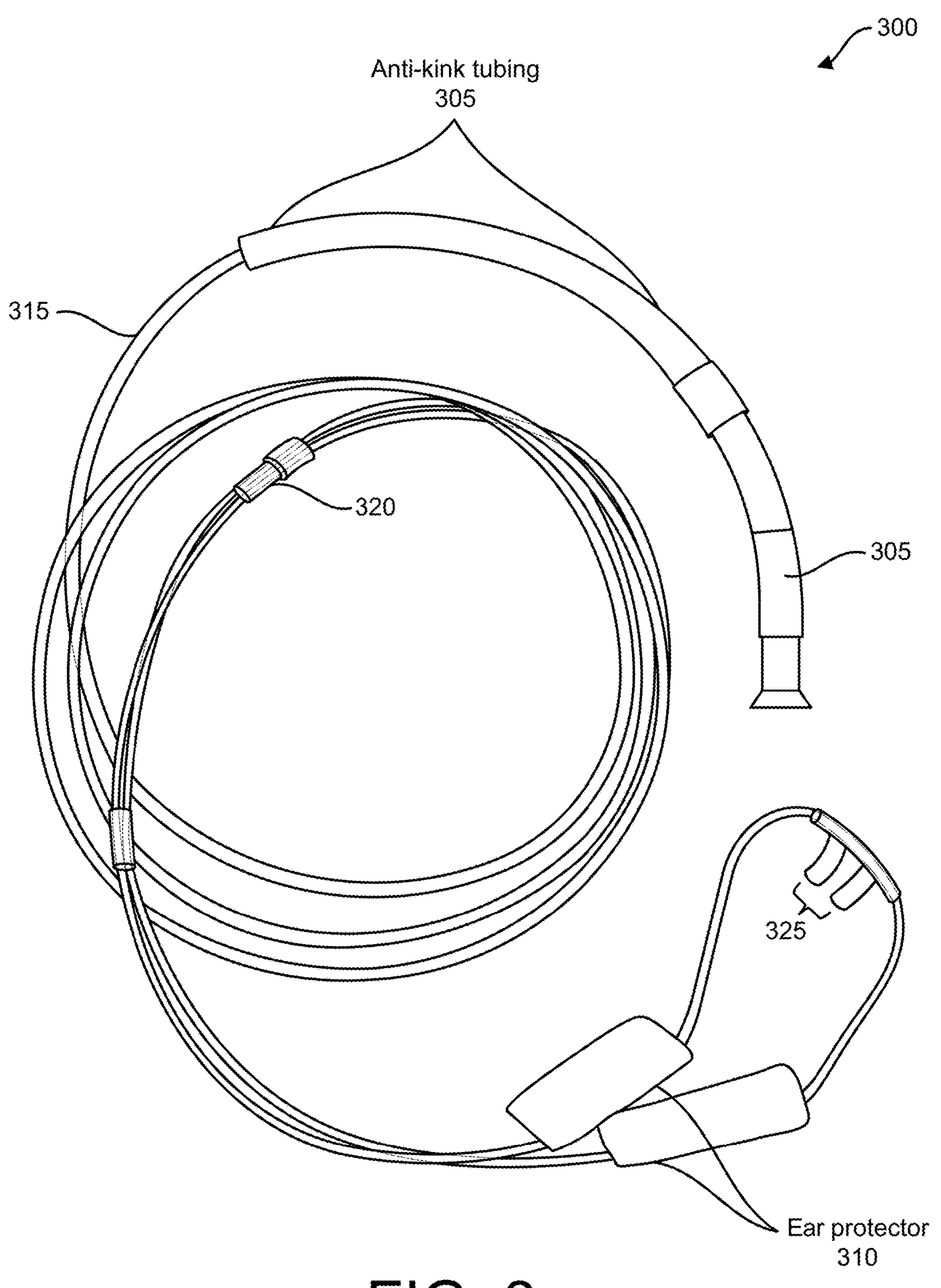
FIG. 3 shows an exemplary embodiment of an anti-kink nasal cannula device combined with ear protectors in accordance with the present invention.
Figure 11:
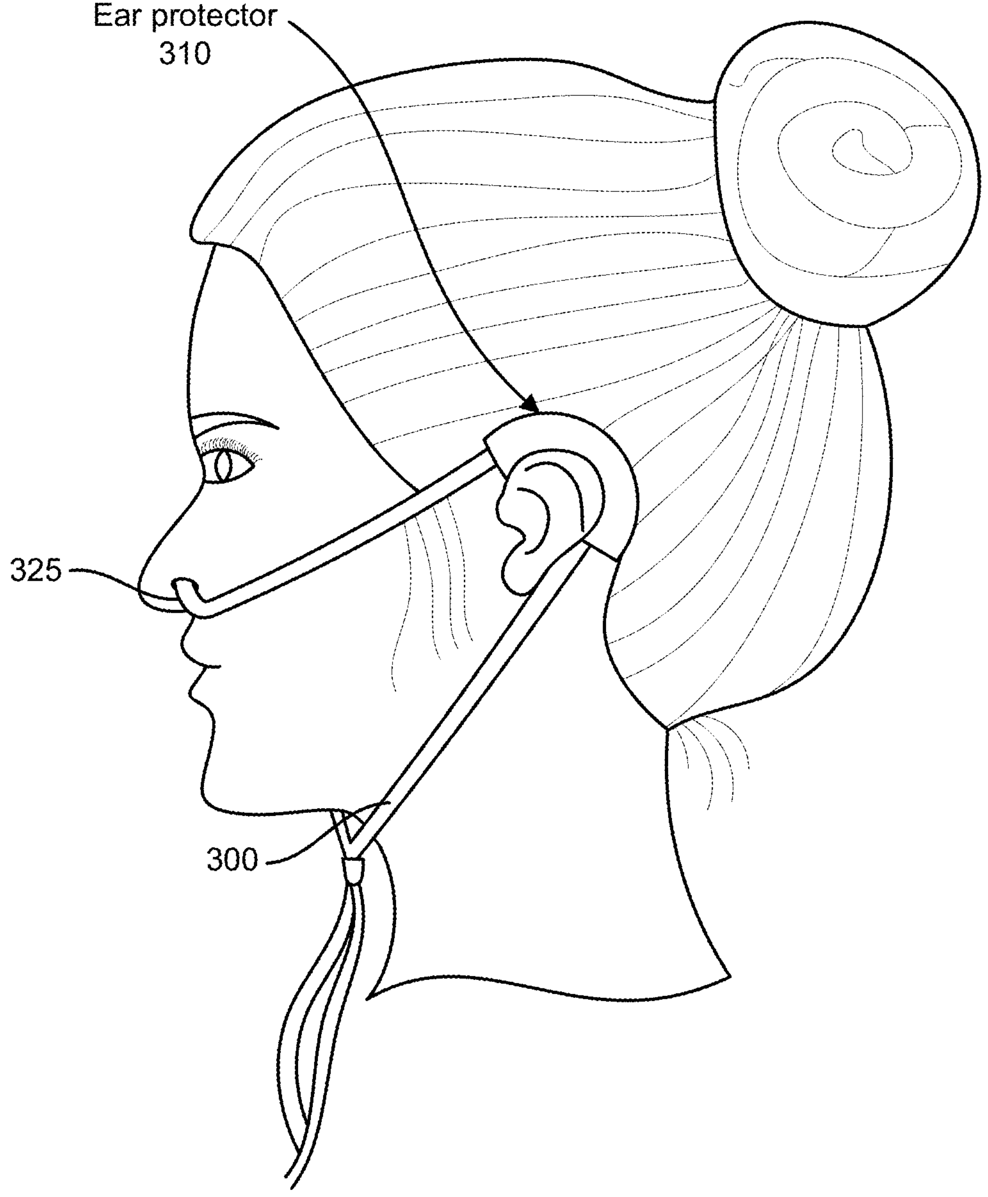
FIG. 11 is a side view of the anti-kink nasal cannula device combined with ear protectors as contemplated by the present invention being used by a patient.

An exemplary embodiment of an anti-kink nasal cannula device in combination with ear protectors 300 that can be used with a portable oxygen system according to the present invention is illustrated in FIGS. 3 and 11. The device 300 can include an anti-kink device 305 and an ergonomically designed ear protection device 310. The anti-kink device 305 and the ear protection device 310 can be made of a wide array of materials, including, but not limited to, silicon, rubber, plastic or other polymer-based materials, or other suitable materials. The nasal cannula, oxygen tubing 315, anti-kink device 305, and ear protection device 310 are soft and flexible as to allow proper comfort by the user.

In various embodiments, the present invention relates to a combined anti-kink nasal cannula device 300 that is ergonomically designed to prevent skin irritation. In some embodiments, the present invention further includes a sensing device 320 to monitor and adjust the oxygen supply delivered to the user, especially during exertion.

The nasal cannula device 300 is a small, flexible tube that contains two open prongs 325 configured to sit just inside a person's nostrils. The tubing 315 attaches to an oxygen source and delivers a steady stream of medical-grade oxygen to the user's nose.

The nasal cannula device 300 is lightweight, easy to use, and affordable. The nasal cannula device 300 is relatively efficient and simple in terms of design and implementation. The nasal cannula device 300 and the oxygen source that it connects to may be used in a variety of hospital settings, at home, or activities in public. In general, nasal cannulas are medical devices used when people are unable to get sufficient oxygen to keep their body functioning optimally, whether that is due to a condition like COPD, another respiratory disorder, or an environmental change.

Various embodiments are directed towards a portable oxygen system. The portable oxygen system is configured to generate a supply of oxygen or oxygen-enriched gas to a respiratory circuit for delivery to an airway of a user who wants portability. For example, in some embodiments, the portable oxygen system may be a portable oxygen tank. In other embodiments, the portable oxygen system may be an oxygen concentrator. Although the present invention is described in a medical setting being used by a patient, one of ordinary skill in the art would understand that the invention may be used for various applications where additional oxygen is needed or desired to help with breathing, for example, for use by a fireman, pilot, paramedic, athlete, or medical responder.

Anti-Kink Device

The present invention is directed to the inclusion of one or more anti-kink devices 305 in connection with the routing of oxygen through the oxygen tube 315 to the user. The present invention provides a breathing tube 315 that is very light, resistant to kinking, and very flexible to ensure the greatest performance and comfort for the patient.

In various embodiments, as shown in FIG. 3, the nasal cannula device 300 includes an anti-kink device 305 configured as a tube sleeve for receiving the oxygen tube 315. One end of the oxygen tube 315 is disposed in the tube sleeve 315 and the other end at prongs 325 delivers oxygen to the user. In FIG. 3, the nasal cannula device 300 has a core oxygen tubing 315 reinforced by an anti-kink device 305 at the oxygen outlet that connects to the Christmas tree adapter 115.

The Christmas tree adapter 115 is used to attach the oxygen tubing 315 to the oxygen source. The Christmas tree adapter 115 includes grooved barbs 125 over which the oxygen tube slides. The tiered barbs 125 of the Christmas tree adapter 115 hold the oxygen tube 315 in place and keep the tube 315 secure. The other end 135 of the Christmas tree adapter includes a nut that can be screwed onto a nipple of the oxygen outlet.

As shown in FIG. 3, the anti-kink device extends over the oxygen tube 315 and conforms to the shape and curve of the oxygen tube. The anti-kink device 315 may cover at least a portion of the oxygen tube. In other embodiments, the anti-kink device 305 may attach at the Christmas tree adapter 135 and extend and attach to the ear protector device to provide reinforcement from the Christmas tree adapter connection to the ear protector 310. In some embodiments, the anti-kink device 305 may be a sleeve integrally formed with the oxygen tube 315. The anti-kink device 305 may be bound to the oxygen tube 315 during the manufacturing process. In further embodiments, the anti-kink device 305 may be configured as a selectively attachable and detachable device in the form of a clip-on sleeve that removably surrounds the oxygen tube 315. The clip-on sleeve can provide tubing support only at the location of the oxygen tube 315 where and when it is needed.

The oxygen tube 315 is protected or shielded against kinking or bending, and it is also strengthened by the anti-kink device which also functions as a strengthener. The anti-kink device prevents bending or twisting of the oxygen tube at the connection to the Christmas tree adapter 135; however, the oxygen tube remains flexible. This is an improvement in comparison to conventional devices wherein the oxygen tube can be twisted, bent, or become kinked at or adjacent to the Christmas tree adapter.

The nasal cannula device 300 can be connected to the Christmas tree adapter 115, which is directly attached to the portable oxygen system. In other embodiments, the portable oxygen system may also include a humidifier that is used for humidifying the oxygen and is connected between the nasal cannula device and the portable oxygen tank.

The anti-kink device 305 can be produced from a variety of methods and materials to reinforce the oxygen tubing 315. The anti-kink device 305 can be configured having various configurations. However, the anti-kink device 305 is designed so that the tube remains lightweight for the user's comfort. The anti-kink device 305 may be configured to be an external support (FIG. 4A), an internal support (FIG. 4B) or a combination thereof. In such an external embodiment in FIG. 4A, the anti-kink device 305*a* is configured to fit on the outer surface of the oxygen tube 315*a*. In an internal embodiment, the oxygen tube 315*b* may include an internal stabilizer 305*b* that provides internal support to center or stabilize the oxygen tube 315*b* to prevent kinking of the oxygen tube 315*b*. In this embodiment, the anti-kink device 305*b* may fit within the inner surface of the oxygen tube 315*b* without obstructing the flow of oxygen to the user.

In an embodiment wherein the anti-kink device 305*a* is designed as an external support, the anti-kink device 305*a* can be a heat shrink tube or a heat shrink sleeve to protect the oxygen tube. The heat shrink provides an additional layer to the oxygen tube. During conventional use, oxygen tubes attached to portable oxygen system are often stretched and experience strain. Theses external tensions can affect the life span of the oxygen tube. The heat shrinks can be incorporated, in various embodiments of the present invention, to reduce these strains and stress applied to the oxygen tube.

During manufacturing, the heat shrink can be positioned to surround the oxygen tube at the desired location, and then heat can be applied to the heat shrink. The dimensions of the heat shrink can be selected based on parameters, such as the inner diameter, shrinkage ratio, length, and thickness. The inner diameter can be selected with a 20%-30% allowance to provide the appropriate space for the heat shrink to merge tightly with the oxygen tube. The heat shrink ratio is the ratio between the inner diameter before heating and the inner diameter after heating. A heat shrink with a high shrinkage ratio is best suitable for surrounding objects such as the connector at the Christmas Tree adapter 115. The high ratio heat shrink can encase the body of the connector and still be able to shrink to a smaller diameter of the oxygen tube. Heating the shrink tube may reduce the length of the tube by 5%-7%. Therefore, the shrink tube should be selected having a length greater than the desired final length. Regarding the thickness, as the tube shrinks, the thickness of the tube increases. The thickness should be selected based on the application.

In some embodiments, the anti-kink device 305 can be configured having a length of approximately 3 inches to about 10 inches, an inner diameter of approximately 0.05 inches to 2 inches, and a thickness of approximately 0.025 mm to 1.25 mm. According to a preferred embodiment, the anti-kink device is configured as a polyolefin heat shrink tubing and has a length of about 8 inches, inner diameter of about 1.1906 mm, and a thickness of about 0.04688 mm. It is noted that one skilled in the art would recognize that the material and/or the dimensions of the anti-kink device can vary depending on the application.

Figure 5A:
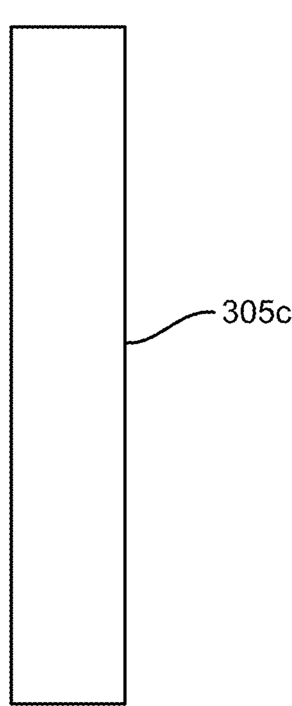
FIG. 5A illustrates an exemplary embodiment of an anti-kink device having a longitudinal configuration in accordance with the present invention.
Figure 5B:
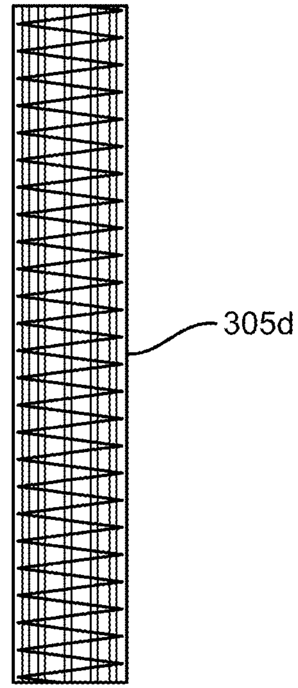
FIG. 5B illustrates an exemplary embodiment of an anti-kink device having a spiral configuration in accordance with the present invention.
Figure 6A:
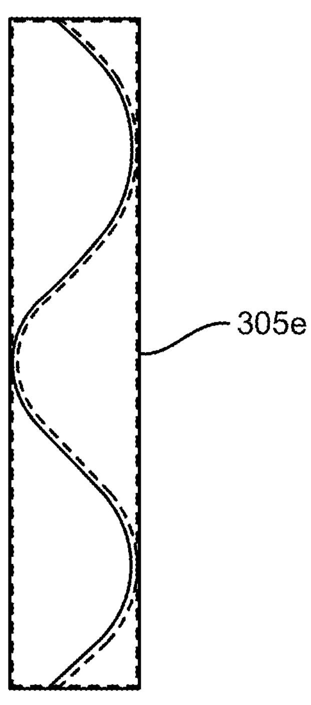
FIG. 6A illustrates an exemplary embodiment of an anti-kink device having a spirally wound configuration in accordance with the present invention.
Figure 6B:
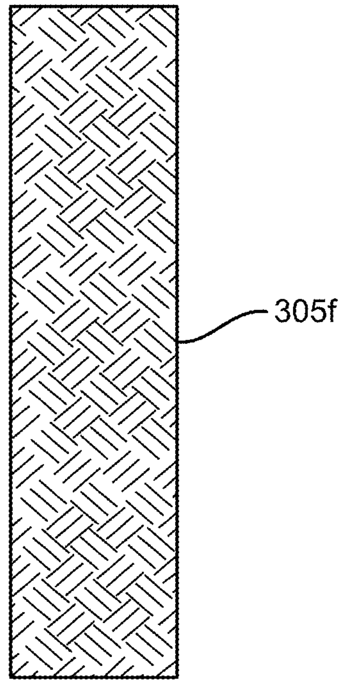
FIG. 6B illustrates an exemplary embodiment of an anti-kink device having a braided configuration in accordance with the present invention.

In various embodiments, constructions of the anti-kink device 305 can include, for example, longitudinal member 305*c* (FIG. 5A), spiral member 305*d* (FIG. 5B), or braided member 305*f* (FIG. 6B) as well as combinations and variations of each. The anti-kink device, in some embodiments, may be designed as a single layer tube. In other embodiments, the anti-kink device may be a multilayer tube. In an alternate embodiment, the features may be combined so that a portion of the tube is a single layer, and another portion is a multilayer. The reinforcing materials can range from high strength polymers to metals, such as copper/copper alloys and stainless steel. The reinforcing wire can be provided within the tube wall to add extra strength and prevent kinking. The reinforcing tube can be produced using all types of wire, tempers, and gauges.

Figure 4A:
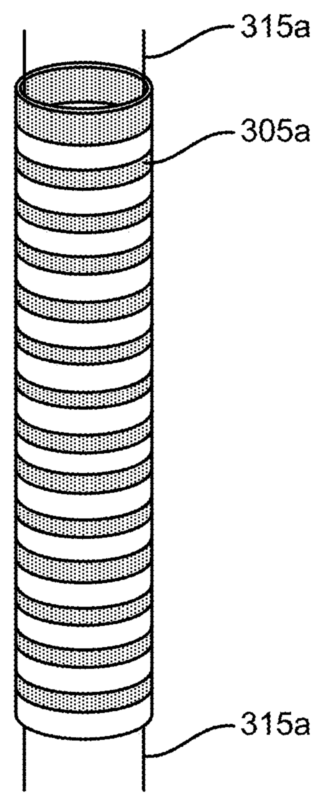
FIG. 4A illustrates an exemplary embodiment of an external anti-kink device in accordance with the present invention.
Figure 4B:
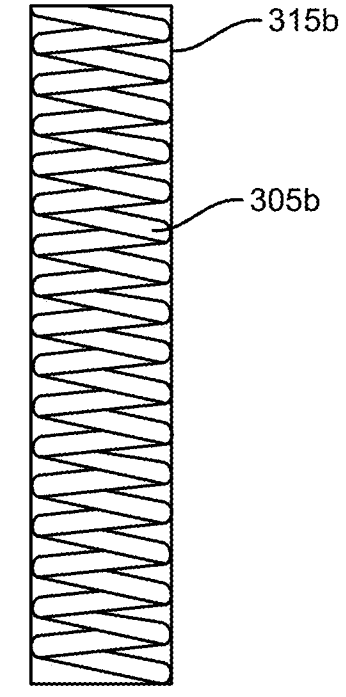
FIG. 4B illustrates an exemplary embodiment of an internal anti-kink device in accordance with the present invention.

For example, in exemplary embodiments of external supports, FIGS. 3 and 4A illustrate an anti-kink device as a longitudinal member that extends lengthwise of a portion of the oxygen tube. The anti-kink device may include a tube sleeve having one or more spirally wound member 305*e* (FIG. 6A) or braided member 305*f* (FIG. 6B) wires or ribs around the circumference. Other example embodiments of the anti-kink device may comprise an external corrugated tube portion.

Figure 8:
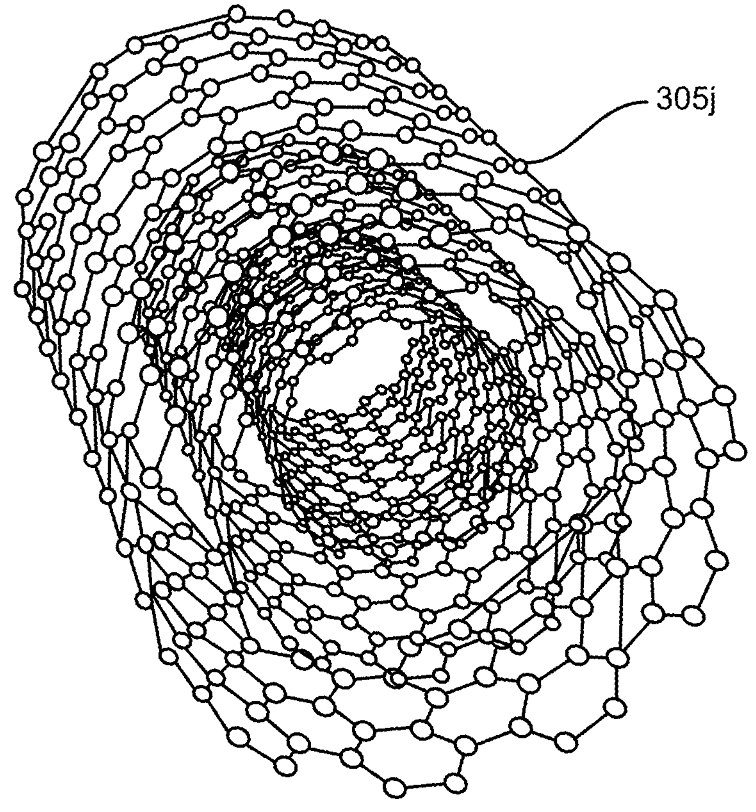
FIG. 8 illustrates an exemplary embodiment of an anti-kink device having a multiple wall configuration in accordance with the present invention.

In some embodiments, the structural reinforcing material of the anti-kink material may include a conductive material, for example, a carbon nanotube. The carbon nanotube combines mechanical, electrical, and thermal characteristics. The anti-kink device can be configured as a single-wall device. In such an embodiment, the anti-kink device can be configured by a single layer that form a hexagonal (honeycomb mesh). In this embodiment, depending on the design of the helical structure, the carbon nanotube can be an armchair structure (FIG. 7A) 305*g*, a zigzag structure 305*h* (FIG. 7B), or a chiral structure 305*i* (FIG. 7A). In other embodiments, the anti-kink device may be configured as a multiple wall device 305*j*, as shown in FIG. 8.

Figure 9:
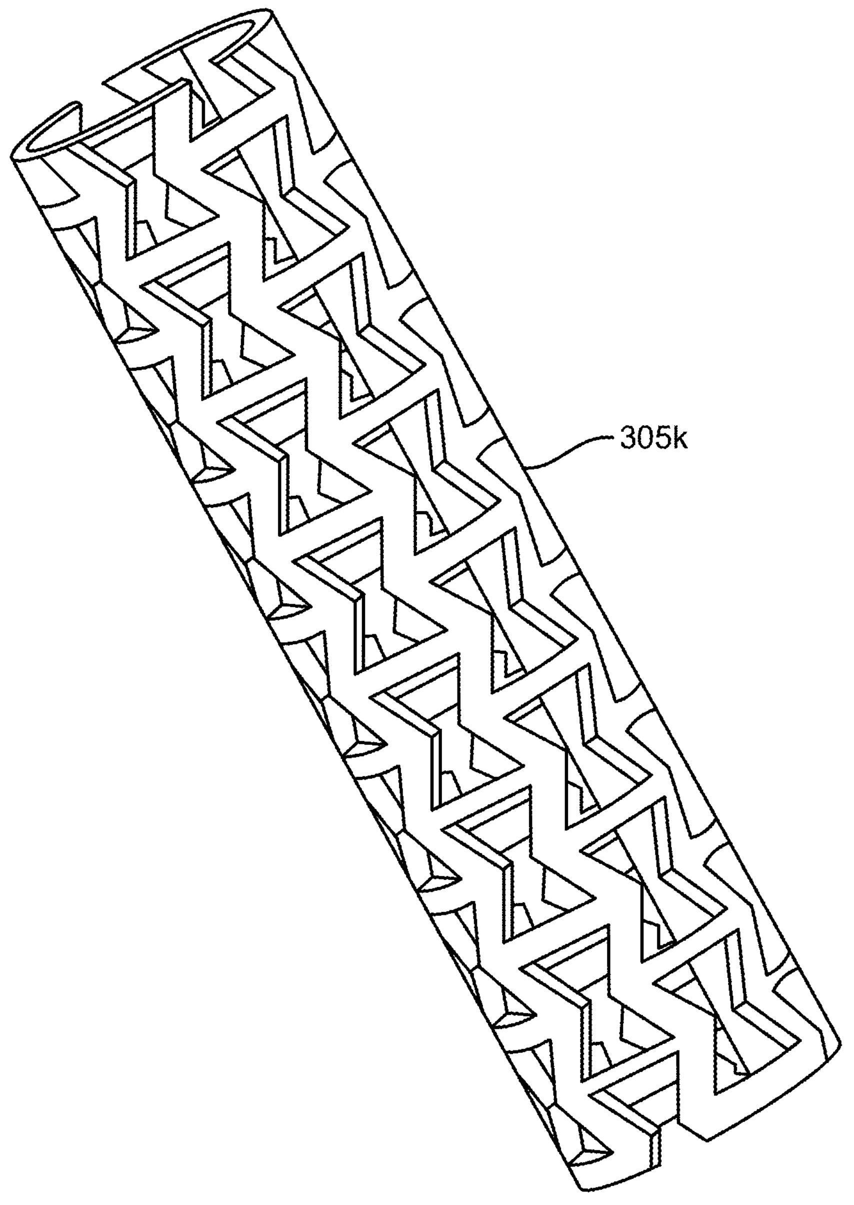
FIG. 9 illustrates an exemplary embodiment of an anti-kink device having an auxetic configuration in accordance with the present invention.

Various embodiments may include one or more auxetic structures 305*k* (FIG. 9) provided within the anti-kink device. Auxetic structures become thicker when stretched and thinner when compressed. The defining property of an auxetic structure is that it possesses one or more negative Poisson's ratios (as opposed to the positive Poisson's ratio displayed by 'normal' materials). This contrasts with 'normal' materials which tend to thin when stretched. The auxetic structures 305*k* can be used in the anti-kink device as a reinforcing support. In the example shown in FIG. 9, the auxetic structure 305*k* is configured by a plurality of generally polygon shapes which resembles an hourglass or bow-tie shape.

In an alternate embodiment, the anti-kink device is a flexible tubular Chinese-finger sleeve made from individual cross-woven strands. The anti-kink device consists of strands that are woven in a helical pattern. The strands may be made of the same material or of different materials. This embodiment operates by a change in the strand angle. Strands of the anti-kink device may have a predetermined cross winding angle within a range of approximately 20° to 60°, preferably 30°. Placing tension on the anti-kink device reduces the angle of the strands, which reduces the cylindrical diameter of the tube of the anti-kink device. The Chinese-finger embodiment converts tension force along the tube of the anti-kink device to a compression force across the oxygen tube through the strands. Because the strands are interlaced, an increase in tension across the strands will cause the anti-kink device to constrict, increasing the gripping force exerted on the oxygen tube.

Figure 10A:
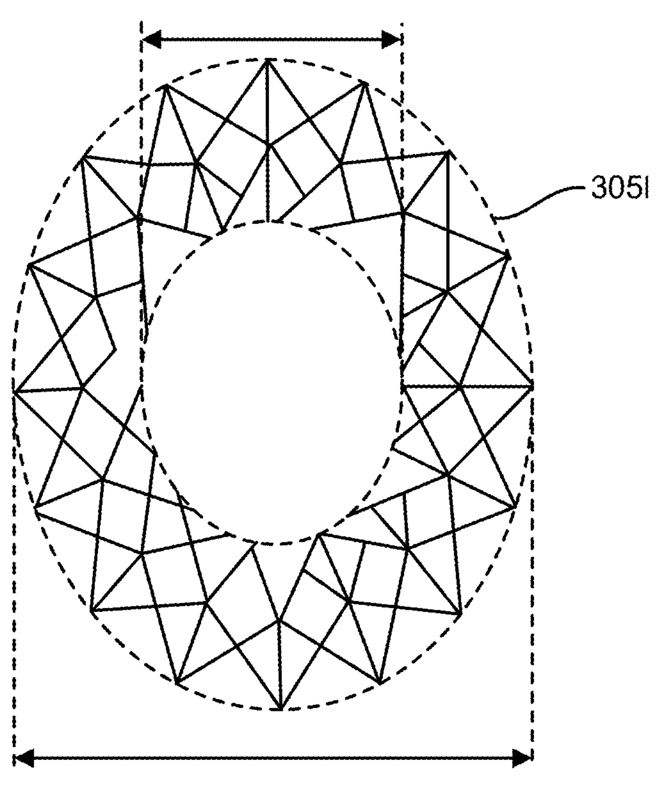
FIG. 10A illustrates an exemplary embodiment of an anti-kink device having a three-dimensional configuration in accordance with the present invention.
Figure 10B:
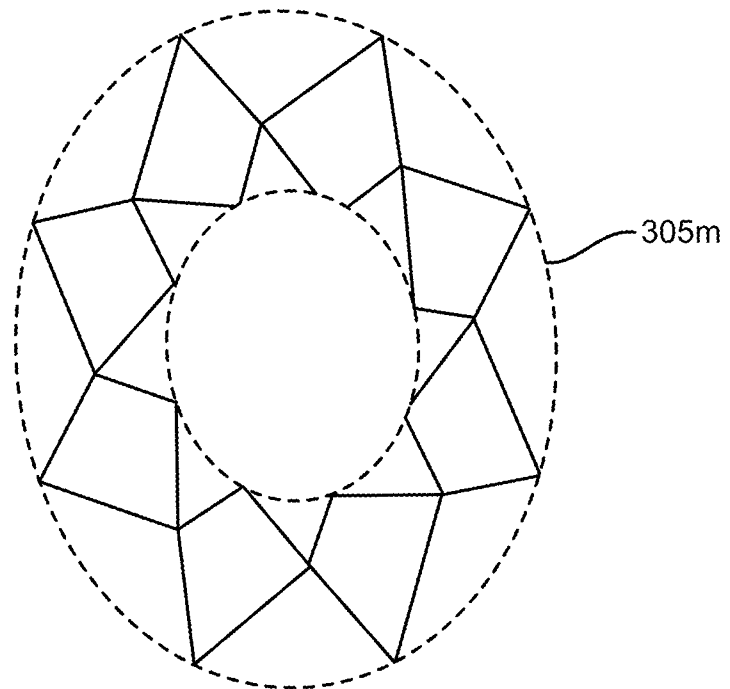
FIG. 10B illustrates another exemplary embodiment of an anti-kink device having a three-dimensional configuration in accordance with the present invention.

In various embodiments, the anti-kink device may include one or more three-dimensional (x, y, z) contour surface geometries 305*l*, 305*m* as shown in FIGS. 10A-10B. The surface of the anti-kink device may include spaced apart uniform or irregular shapes including nodules, denticles, bumps, or protuberances.

In various embodiments where the anti-kink device is removably attached to the oxygen tube at the connection of the Christmas tree adapter, the anti-kink device may include at least one high-friction area within the inner surface. The high-friction area may be defined by multiple gripping members. When the anti-kink device is positioned over the oxygen tube, the gripping member remains in contact with the desired areas of the oxygen tube due to the frictional force. The frictional forces counteract against outside forces that would otherwise cause the oxygen tube to kink. Gripping members of the present invention may be of any suitable size. The gripping members can be any type of nodules, ribs, and protrusions on the inner surfaces of the anti-kink device for aiding in securing the anti-kink device to the oxygen tube and to prevent kinking of the oxygen tube.

In the three-dimensional embodiments, the anti-kink device may include one or more three-dimensional (3-D) projections 305*l*, 305*m* configured to house and retain one or more sensor wires therein.

Ear Protector/Ergonomic/Comfort

One or more embodiments of the present invention provides an ear protection device 310 as illustrated in the example in FIGS. 3 and 11 to enhance comfort during use of the nasal cannula 300. During use of some conventional oxygen tubes, the oxygen tube can twist bend or otherwise move or deform in a manner that can cause discomfort, pain, skin irritation and possibly even infection of the user's ear. Thus, the present invention provides ear protection devices 310 formed of a soft, resilient material to enhance comfort. Thus, a potential source of discomfort, skin irritation, pain, is mitigated.

In some embodiments, the ear protection device 310 is designed to cover the portion of the oxygen tube 315 that loops behind the user's ears when wearing the oxygen nasal cannula device 300. In other embodiments, the ear protection device 310 can be designed to cover the loops that extend behind the user's ears. In another embodiment, the ear protection device 310 can be used by patients who wear eyeglasses. The ear protection device can cover at least a portion of the temples of the eyeglasses, which connect and hold the frames to the wearer's head, behind and below the ears.

The ear protection device 310 can be configured to have soft surfaces that are comfortable when in contact with a user's ear, are reusable, and may be conveniently cleaned with soap and warm water. In various embodiments, the ear protection device 310 is a sleeve formed of a soft, pliable, shape-retaining, antimicrobial/antibacterial material, which is biocompatible to allow contact with the user's ear. The sleeve fits permanently or temporarily around the oxygen tube.

The ear protection devices 310 can be made of any suitable material to improve patient comfort and wearability of the nasal cannula device 300. In some embodiments, the oxygen tube 315 can be overmolded with a softer material. In other embodiments, a soft material can be selectively attached to the oxygen tube 315 as a clip-on sleeve or by Velcro™ In both embodiments of the present invention, the ear protection devices 310 are designed to stay in place and not slip down or fall off the oxygen tube, which is a disadvantage associated with some conventional ear protectors, such as the E-Z Wrap Soft Form Ear Protectors for Oxygen Nasal Cannulas. The soft material of the ear protection device 310 may consist of a fabric, foam, cotton, polyester, plastic, polymer, or other like material. The material of the ear protection device 310 can include elastomeric properties that minimizes friction and shear forces against the user's skin. Additional embodiments can use one or more alternative closing mechanisms such as magnetic materials/magnetic dust/magnet(s), button(s) snap(s), hook(s) and loop(s), elastic(s), zipper(s), string(s), fabric, knit tubing/knitted material(s) and the like, as long as the closing mechanism does not cause the user discomfort.

To provide comfort for contacting the patient's skin, the material of the ear protection device 310 breathes, wicks moisture away from the skin for enhanced comfort. In addition, the ear protection device 310 may include one or more characteristics or properties, such as venting, moisturizing, and lubricating.

In general, the ear protectors 310 can include materials for softening contact of the ear protectors 310 against the user's ear. The materials are intended to provide comfort to the user as the ear protectors are used and to reduce skin irritation. In one preferred embodiment, the ear protectors are made from a 100% polyester fiber weighing about 0.06 ounces and having a length of 2.5 inches and a width of 1.25 inches to surround and encase the oxygen tube.

In some embodiments, the ear protectors can be configured to possess enough rigidity to properly conform to the user's ear and to sure an ear probe to the user's ear. Various embodiments of the invention provide one or more sensors that directly contact a tissue of the user to take oxygen saturation measurements of the tissue. In some embodiments, the one or more sensors can be configured as a biosensor, such as an ear probe included within the ear protection devices 310. The biosensors can be used to detect the presence or concentration of a biological analyte, such as a biomolecule, a biological structure, or a microorganism. The biosensor can consist of at least three parts: a component that recognizes the analyte and produces a signal, a signal transducer, and a reader device.

In various embodiments, the ear protection device 310 can be made of a conductive material or fabric, such as a carbon nanotube, as described above in FIGS. 7A-8. In such an embodiment, the conductive material or fabric can be useful for a wearable biological information device capable of measuring biological information, such as respiration rate, body temperature, and the like by being in contact with the user.

Monitoring

In further embodiments, the present invention may include one or more sensor cables 320 or sensor wires that carry signals, for example, for sensing air flow or pressure flowing through the oxygen 315 tube for monitoring and adjusting the oxygen supply to maintain the level prescribed by the user's physician, even during exertion.

The present invention combines the supply of oxygen or oxygen-rich air with a sensing device that adjusts the oxygen supply to better match the actual body requirement based on the measured blood oxygen saturation. The present invention is configured to supply the user with a sufficient amount of respiratory airway pressure in order to maintain the required level of air volume in the lungs, even during exertion.

In one embodiment, the anti-kink device 305 and/or ear protection device 310 is configured with one or more sensors. The one or more sensors may be configured to monitor and measure flow, pressure, and other information. The sensors can be coupled wirelessly to provide real time information about the flowrate, pressure, identification, location, and other information for the patient. In further embodiments, the one or more sensors can be configured to wireless communicate with another device, such as the flowmeter. For example, a sensor can be positioned at the connection of the anti-kink device 305 at the Christmas tree adapter 115 that is in communication with the ear probe sensor installed within the ear protection device.

In various embodiments, the present invention is directed towards a portable oxygen tank system that is mainly composed of an oxygen tank, an oxygen regulator, pressure gauge, and a flow meter. The oxygen tank can be a metal tank that keeps the oxygen under pressure. The pressure gauge indicates how much oxygen remains in the tank. The flow meter controls the rate (how fast) the oxygen comes out of the tank. In embodiments including a humidifier, the humidifier contains water that is mixed with the oxygen, and the oxygen is warmed before the patient breathes it. The humidifier helps to prevent the patient's nose, mouth, and throat from becoming too dry.

In other embodiments, the present invention is directed towards a portable oxygen concentrator that typically includes a compressor, absorption columns with air filters, circuitry, a product tank, and regulator. Oxygen concentrators differ from machines delivering compressed oxygen from tanks which are filled at a separate location. Instead, an oxygen concentrator takes standard room air, separates oxygen from the nitrogen and other gases, leaving oxygen to be delivered to the patient. For instance, when set at a rate of two liters per minute, the gas that is delivered by the concentrator to the patient is more than 90% oxygen.

According to the present invention, in use with either the oxygen tank system or the oxygen concentrator, pressure and oxygen sensors can be used at various points to ensure proper creation and delivery of oxygen. For example, an oxygen sensor can be installed to sense the oxygen percentage of the air being delivered to the patient. A pressure sensor can be used at the product tank to measure the tank's level and to ensure there is proper flow moving into the regulator. In addition to the anti-kink device, a pressure sensor can be located between the regulator and oxygen outlet to detect a kink in the tubing. In some embodiments, the pressure sensor can be used to detect inhalation which then controls the regulator.

Some conventional portable oxygen systems use real-time pulse oximetry to monitor blood oxygen levels. However, when the user's blood oxygen level decreases and needs to be adjusted, these conventional devices are unable to detect whether the decrease in oxygen level is due to kinking of the tube or the patient's medical condition. Thus, the anti-kink device 305 of the present invention can be attached to the oxygen tubing of conventional portable oxygen systems to ensure that the user's decrease in saturation of oxygen is actually the result from a patient's medical problem and not related to a kink in the tubing or some type of tubing flow defect.

According to the present invention, the system may include a processing unit for processing signals, for example, from the circuitry within the portable unit and sensing devices located along the oxygen tube.

The foregoing detailed description of one or more exemplary embodiments of the portable oxygen system including a nasal cannula device has been presented herein by way of example only and not limitation. It will be recognized that there are advantages to certain individual features and functions described herein that may be obtained without incorporating other features and functions described herein. Moreover, it will be recognized that various alternatives, modifications, variations, or improvements of the above-disclosed exemplary embodiments and other features and functions, or alternatives thereof, may be desirably combined into many other different embodiments, systems, or applications. Presently unforeseen or unanticipated alternatives, modifications, variations, or improvements therein may be subsequently made by those skilled in the art which are also intended to be encompassed by the appended claims. Therefore, the spirit and scope of any appended claims should not be limited to the description of the exemplary embodiments contained herein.

What is claimed is:

1. A nasal cannula device, comprising:

a flexible tube having an inner surface and an outer surface;

one or more anti-kink devices attached to a distal end of the flexible tube that connects to a connection adapter, so that the one or more anti-kink devices provide support to the flexible tube to prevent kinking of the flexible tube;

one or more ear protection devices attached to or integral with a portion of the flexible tube that is configured to contact a user's ear, wherein the one or more ear protection devices comprise a soft material to mitigate skin irritation of the user's ear;

wherein the one or more anti-kink devices extend from the connection adapter and attach to the one or more ear protection devices and wherein the one or more anti-kink devices are configured to be selectively attachable and detachable to surround and conform to and prevent kinking along the flexible tube;

a plurality of pressure sensors disposed within the one or more anti-kink devices and configured to monitor and measure pressure, wherein at least one sensor of the plurality of pressure sensors is configured to detect a kink in the flexible tube; and;

a processing unit in communication with the plurality of pressure sensors, wherein the processing unit is configured to receive and process signals generated by the at least one sensor of the plurality of sensors to detect the kink in the flexible tube.

2. A nasal cannula device for delivering breathing gas, comprising:

a flexible tube having an inner surface and an outer surface;

one or more anti-kink devices attached to a distal end of the flexible tube that connects to a connection adapter, so that the one or more anti-kink devices provide support to the flexible tube to prevent kinking of the flexible tube;

one or more ear protection devices attached to or integral with a portion of the flexible tube that is configured to contact a user's ear, wherein the one or more ear protection devices comprise a soft material to mitigate skin irritation of the user's ear;

wherein the one or more anti-kink devices extend from the connection adapter and attach to the one or more ear protection devices and wherein the one or more anti-kink devices are configured to be selectively attachable and detachable to surround and conform to and prevent kinking along the flexible tube;

a plurality of first sensors disposed within the one or more anti-kink devices and configured to monitor and measure pressure, wherein at least one of the plurality of first sensors comprises a pressure sensor configured to detect a kink in the flexible tube;

at least one second sensor positioned proximate the one or more ear protection devices, the at least one second sensor configured to detect a biological analyte on the user's skin; and a processing unit in communication with the plurality of first sensors and the at least one second sensor to monitor and adjust an oxygen level to maintain a predetermined oxygen supply delivered to a user during movement and exertion; and wherein the processing unit is configured to receive and process signals generated by the at least one sensor of the plurality of first sensors to detect the kink in the flexible tube.

3. The nasal cannula device of claim 2, wherein the one or more anti-kink devices is a clip-on sleeve.

4. The nasal cannula device of claim 2, wherein the one or more anti-kink devices comprises at least one of a single layer anti-kink device, a multiple layer anti-kink device or a combination thereof.

5. The nasal cannula device of claim 2, wherein the one or more anti-kink devices comprises at least one of an internal support anti-kink device, an external support anti-kink device or a combination thereof.

6. The nasal cannula device of claim 2, wherein the one or more anti-kink devices is selected from the group consisting of a spiral structure, a braided structure, a hexagonal structure, a helical structure, an armchair structure, a chiral structure, or any combination thereof.

7. The nasal cannula device of claim 2, wherein the one or more anti-kink devices comprises a carbon nanotube configured to combine and impart mechanical, electrical, and thermal properties to the one or more anti-kink devices.

8. The nasal cannula device of claim 2, wherein the one or more anti-kink devices comprises an auxetic structure having a negative Poisson's ratio such that, when stretched, a width of the auxetic structure increases and becomes thicker perpendicular to an applied force.

9. The nasal cannula device of claim 2, wherein the one or more anti-kink devices comprises a plurality of interlaced strands having a predetermined angle woven together to form a Chinese finger sleeve wherein a tension force applied to the Chinese finger sleeve reduces the angle of the strands and increases a gripping force exerted on the flexible tube.

10. The nasal cannula device of claim 2, wherein the one or more anti-kink devices comprises one or more three-dimensional (3-D) projections configured to house and retain one or more sensor wires therein.

11. The nasal cannula device of claim 2, wherein the soft material of the ear protection device is selected from the group consisting of fabric, foam, cotton, polyester, plastic, polymer, or any combination thereof.

12. The nasal cannula device of claim 2, wherein the soft material of the ear protection device is a material that is configured to wick moisture away from the user's skin.

13. The nasal cannula device of claim 2, wherein the at least one second sensor comprises one or more biosensors including one or more ear probes for detecting one or more physiological conditions.

14. The nasal cannula device of claim 2, wherein the soft material of the ear protection device comprises a wearable, flexible conductive material or fabric for sensing biological information about the user.

15. The nasal cannula device of claim 2, wherein the at least one second sensor is configured to detect an oxygen saturation measurement of the user.

16. The nasal cannula device of claim 15, wherein the processing unit is configured to, in response to receiving the sensor data from the plurality of first sensors and the at least one second sensor, determine that a decrease in the oxygen saturation measurement results from a medical condition of the user and not from a tubing flow defect in the flexible tube.

17. A nasal cannula device for delivering breathing gas, comprising:

a flexible tube having an inner surface and an outer surface;

one or more anti-kink devices attached to a distal end of the flexible tube that connects to a connection adapter, so that the one or more anti-kink devices provide support to the flexible tube to prevent kinking of the flexible tube;

one or more ear protection devices attached to or integral with a portion of the flexible tube that is configured to contact a user's ear, wherein the one or more ear protection devices comprise a material to mitigate skin irritation of the user's ear;

wherein the one or more anti-kink devices extend from the connection adapter and attach to the one or more ear protection devices and wherein the one or more anti-kink devices are configured to be selectively attachable and detachable to surround and conform to and prevent kinking along the flexible tube;

a plurality of first sensors disposed within the one or more anti-kink devices and configured to monitor and measure pressure, wherein at least one of the plurality of first sensors comprises a pressure sensor configured to detect a kink in the flexible tube;

at least one second sensor included in the one or more ear protection devices, the at least one second sensor configured to detect a biological analyte on the user's skin;

a processing unit in communication with the plurality of first sensors and the at least one second sensor to monitor and adjust an oxygen level to maintain a predetermined oxygen supply delivered to a user;

wherein the processing unit is configured to receive and process signals generated by the at least one sensor of the plurality of first sensors to detect the kink in the flexible tube;

wherein the processing unit is configured to, in response to receiving sensor data from the plurality of first sensors and the at least one second sensor, determine whether a decrease in an oxygen saturation measurement of the user results from a medical condition of the user or from a tubing flow defect in the flexible tube;

wherein the at least one second sensor is configured to detect the oxygen saturation measurement of the user; and wherein the at least one second sensor includes a wearable biological information device capable of continuously monitoring and measuring the biological analyte.

18. The nasal cannula device of claim 17, wherein the wearable biological information device is made of a conductive material.

19. The nasal cannula device of claim 18, wherein the conductive material is a carbon nanotube.

* * * * *